United States Patent [19]

Gillette, Jr. et al.

[11] 4,427,304
[45] Jan. 24, 1984

[54] METHOD FOR CRYOGENIC PROOF TESTING OF ROTATING PARTS

[75] Inventors: Frank C. Gillette, Jr., Lake Park; Ernest C. Bryan, Tequesta; Douglas H. Nethaway, Stuart, all of Fla.

[73] Assignee: United Technologies Corporation, Hartford, Conn.

[21] Appl. No.: 366,114

[22] Filed: Apr. 7, 1982

[51] Int. Cl.³ ........................................... G01N 25/00
[52] U.S. Cl. ..................................... 374/46; 148/125
[58] Field of Search .................. 148/125; 73/116; 374/45, 46, 47

[56] References Cited

U.S. PATENT DOCUMENTS 3,250,901  5/1966  Brahm ............................ 73/117.2 X
3,516,874  6/1970  Maker et al. .............................. 148/4
3,615,921  11/1968  Delgrosso ............................ 148/125
3,950,985  4/1976  Buchwald et al. ..................... 73/116
4,046,002  9/1977  Murphy et al. ........................ 374/47

*Primary Examiner*—Herbert Goldstein
*Attorney, Agent, or Firm*—Robert C. Walker

[57] ABSTRACT

A method to test a rotating metal part at a cryogenic temperature as a comprehensive non-destructive inspection technique is disclosed. This method for proof testing a rotating metal part was arrived at for a material which has the characteristics of high strength and low fracture toughness at an operating temperature and when placed at a cryogenic temperature, the strength of the material is increased and the fracture toughness is decreased.

6 Claims, 2 Drawing Figures

METHOD FOR CRYOGENIC PROOF TESTING OF ROTATING PARTS

The Government has rights in this invention pursuant to Contract No. F33657-79-C-0002, awarded by the Department of the Air Force.

Cross Reference

This invention is related to the invention dislosed in co-pending application Ser. No. 366,115 entitled "Apparatus for Cryogenic Proof Testing of Rotating Parts", filed by John F. Schratt and Joseph J. Weber on even date and assigned to the same assignee of this application.

DESCRIPTION

1. Technical Field

This invention relates to a method of cryogenic proof testing of rotating parts and particularly to rotating parts such as engine discs and blades of aircraft. As is well known in the gas turbine engine art, the durability of engine components is of paramount importance and, obviously the longer an engine component endures, the longer an engine can perform without the costly removal of an engine necessitated by the repair or replacement of such components. Presently, for example, the maintenance plan for engine discs requires retirement of a part much sooner than necessary. Current inspection procedures are fluorescent penetrant, eddy current and sonic non-destructive tests which may typically provide for an expectant life of 1400 hours; whereas, cryogenic proof test will allow part usage to 2400 hours. In addition, current inspection methods are susceptible to human error due to the nature of these inspection methods; whereas, cryogenic proof test is essentially foolproof since it is dependent upon the material characteristics, part configuration, and the magnitude of loading during the test.

2. Background Art

U.S. Pat. Nos. 3,250,901 and 4,046,002 show systems for indicating the service operational life of an engine part such as a rotor. U.S. Pat. Nos. 3,273,636 and 3,465,569 set forth two types of chambers which include the use of a cryogenic fluid to control the temperature therein.

Disclosure of Invention

It is an object of this invention to provide a method for cryogenic proof testing a rotatable metallic part while it is rotating as a comprehensive non-destructive inspection technique to eliminate the need for currently less comprehensive in-serivce inspection techniques.

Another object of this invention is to provide a method for proof testing a rotatable metallic part formed of a metal having characteristics of high strength and low fracture toughness, said metal increasing its strength and decreasing its fracture toughness substantially when placed at a cryogenic temperature; said method placing said metallic part at a cryogenic temperature to reduce critical flaw size necessary for part fracture and then rotating said part at said cryogenic temperature and at a speed equivalent to its yield strength so that no permanent deformation of said part occurs while producing a stress on said part to fracture said part at or above the reduced critical flaw size.

A further object of this invention is to provide a proof test method for spinning a part in a cryogenic atmosphere to gain a life benefit due to beneficial residual stresses remaining after the proof test. This will permit the inspection interval of such parts to be increased.

BEST MODE FOR CARRYING OUT THE INVENTION

In view of the fact that current inspection methods used on critical parts of aircraft, a critical part being a part whose failure could jeopardize flight safety, are susceptible to human error due to the nature of the inspection method, a test was sought which would be essentially foolproof and which would depend on the material characteristics of the part. A method of proof testing a rotatable metallic part was determined for a material which has the characteristics of high strength and low fracture toughness at operating temperature of the metallic part, and when the metallic part is placed at a cryogenic temperature, the strength of the material is increased a substantial amount and the fracture toughness is decreased a substantial amount. When a part having these characteristics is placed at a cryogenic temperature, it will rupture at a reduced critical flaw size at operating stress caused by operating speed; and when said part is cooled to a cryogenic temperature and run at a test speed increasing its test stress, the part will rupture at a still reduced critical flaw size.

To achieve the maximum safety limit for testing, the part at cryogenic temperature is rotated at an increased speed which will placed said part under a stress which is just below a point where permanent deformation occurs; at this stress said part will rupture at a greatly reduced flaw size which will provide a safety limit to permit the part to be reused until a subsequent test.

Figure 2:
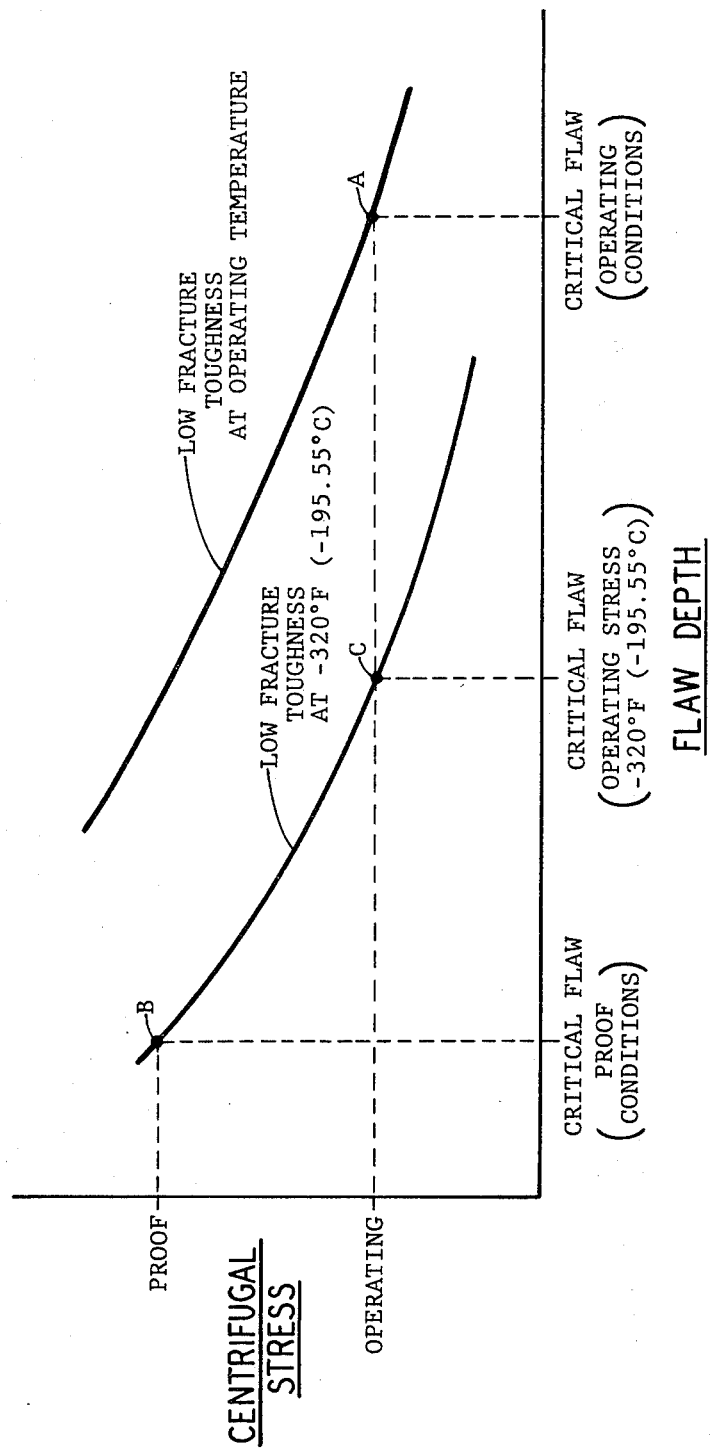
FIG. 2 is a graph showing centrifugal stress plotted against flaw depth for a metal having characteristics of high strength and low fracture toughness at operating temperatures and wherein said strength is increased and fracture toughness decreased at a cryogenic temperature with curves thereon representing low fracture toughness at operating temperature and at $-320°$ F. ($195.55°$ C.).

It can be seen from FIG. 2 that the critical flaw size as represented by critical flaw depth required for fracture of a part at operating temperature and operating centrifugal stress represented by A is much larger than the critical flaw depth required for fracture of a part at a cryogenic temperature of $-320°$ F. ($-195.55°$ C.) and a proof centrifugal stress which is equivalent to 0.2% yield strength of the metal providing no permanent deformation represented by B. In FIG. 2 assuming for a given metal part the critical flaw depth at A to be approximately 0.10 inches (0.254 cm) and the critical flaw depth at B to be approximately 0.003 inches (0.0076 cm), the ratio in critical flaw depths is approximately 1 to 33, a substantial safety limit.

If the given metal part is cryogenically proof tested using these figures, all flaws represented by flaw depth at a predetermined critical location having a depth of 0.003 inches (0.0076 cm) or over, would rupture, leaving the part with only flaws, if any, in that location of under 0.003 inches (0.0076 cm). Using known state-of-the-art methods, the remaining life of the part can be predicted using its operating conditions. The part can be scheduled for cryogenic retesting before the time for anticipated rupture.

Using the same given metal part, in FIG. 2, the operating centrifugal stress would fracture a part at C when the part is at a cryogenic temperature of −320° F. (−195.55° C.). Using the assumptions made above, C represents a critical flaw depth of approximately 0.05 inches (0.127 cm). The ratio in critical flaw depths between C and A is 1 to 2, a low safety limit, too low to provide an adequate test for a part whose failure could jeopardize flight safety. It is therefore advisable to test at a speed equivalent to a stress level at or near 0.2% yield strength for a maximum safety limit. It is to be recognized that a rotating part having a permanent deformation placed therein by speeds equivalent to stress levels above 0.2% yield strength is not acceptable in a quality rotating part.

A specific metal Ti 6-2-4-6 (PWA-1216) had its ultimate tensile strength increase from around 160 ksi at 65° F. (18.33° C.) to around 240 ksi at −320° F. (−195.55° C.) and fracture toughness decrease from around 25 at 65° F. (18.33° C.) to around 15 at −320° F. (−195.55° C.). Parts were successfully tested with this material using the method set forth herein.

A specific metal IN 100 (PWA-1074) had very little increase in strength when placed at −320° F. (−195.55° C.), approximately 20 ksi, and essentially no decrease in fracture toughness. To one skilled in the art, these characteristics do not provide the changes necessary in going from operating temperature to a cryogenic temperature which will detect smaller critical flaws in an efficient manner. Since an object of the invention is to extend time between inspections for cracks, a metal providing little or no increased time period would not be an acceptable metal on which to use this method.

Figure 1:
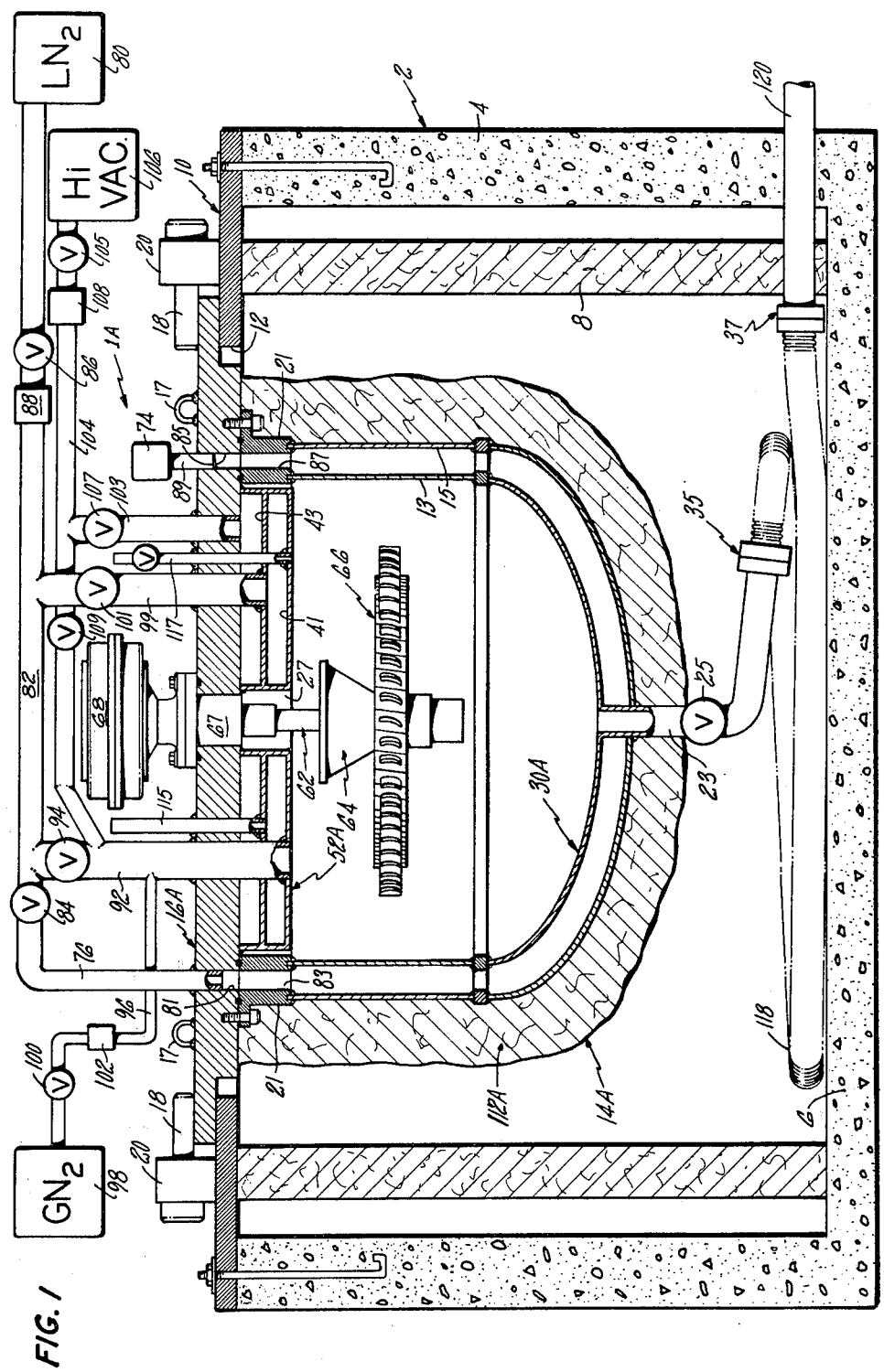
FIG. 1 is a sectional view of a test spin pit containing a cryogenic spin testing chamber with means for obtaining a proper cryogenic temperature therein.

As seen in FIG. 1, a test spin apparatus 1A is shown. The outer container structure includes a spin pit 2 and reinforced concrete and steel containment wall 4 and bottom pad 6. A wall 8 also absorbs energy within the wall 4. The steel top 10 has its outer edge secured to the top of the containment structure 2. A cover 16A is positioned over an opening 12 in the top 10 and is held in position by lock pins 18 in bosses 20 fixed to the steel top 10.

The cryogenic spin testing chamber 14A consists of a double walled container 30A having an inner wall 13 and an outer wall 15. The open ends of the double walls are fixed to an annular ring 21 which is bolted to the bottom of the cover 16A. O-rings are placed between the mating surface of the annular ring 21 and the undersurface of the cover 16A to provide for sealing therebetween. Insulating material 112A is placed around the outer wall 15 of the double walled container 30A. A drain pipe 23 extends from inner wall 13 through outer wall 15 to a point below the insulating material 112A. A remotely operated valve 25 is located in said drain pipe 23. Pipe 23 is sealed with outer wall 15.

Cover 16A has a container insert 52A extending downwardly therefrom which fits into the inner opening of annular ring 21. Container insert 52A is formed having a central opening 27. The container insert 52A is also formed having two annular chambers 41 and 43. Opening 27 accommodates the extension of a rotating shaft means 62. This shaft means 62 is connected to a spin arbor 64 which is adapted to hold a test disc 66.

The rotating shaft means 62 extends through a lateral displacement vibration damper 67 having a vacuum seal contacting rotating shaft means 62. Damper 67 is fixedly positioned in an opening in cover 16A, which is aligned with opening 27 in contained insert 52A. A drive means 68 (such as an air turbine or electric motor) is drivingly connected to rotating shaft means 62 to provide for the rotation. The drive means 68 is vacuum sealed to the cover 16A.

A liquid nitrogen tank 80 has a conduit 82 connected to a conduit section 76 by valve 84; connected to a conduit section 92 by valve 94; and connected to a conduit section 99 by valve 101. To direct liquid nitrogen between the inner wall 13 and outer wall 15, conduit section 76 is connected by a passageway 81 in cover 16A and aligned passageway 83 in annular ring 21 to connect it to the interior of the space between inner wall 13 and outer wall 15. The space between the outer wall 15 and inner wall 13 is connected by a passageway 87 in annular ring 21, passageway 85 in cover 16A, and conduit 89 to a pressure vent and cryogenic fluid level indicator 74. To direct liquid nitrogen into the space between walls 13 and 15 of the double walled container 30A, conduit section 92 passes through and is sealed with cover 16A and the two annular chambers 43 and 41 of the container insert 52A. To direct liquid nitrogen into annular chamber 41, conduit section 99 passes through and is sealed with cover 16A and annular chamber 43 of the container insert 52A. An on-off valve 86 is located in line 82 adjacent the liquid supply tank 80 and a connect-disconnect means 88 is located between valve 86 and the connection of conduit section 99.

A gaseous nitrogen supply tank 98 has a conduit 96 connected to conduit section 92 downstream of valve 94. A valve 100 is located in conduit 96 and a connect-disconnect means 102 is located between valve 100 and the connection of conduit 96 to conduit section 92. This permits gaseous nitrogen to be directed inside wall 13 of the double walled container 30A when desired.

A vacuum pumping device 106 has a conduit 104 connected to conduit section 92 downstream of valve 94. A conduit 103 is connected to conduit 104 while its other end passes through and is sealed with cover 16A to be connected to annular chamber 43. A valve 109 is located in conduit 104 between the point where it is connected to conduit 92 and the connection of conduit 103; and a valve 107 is located in conduit 103. A valve 105 is located in conduit 104 adjacent the vacuum pumping device 106 and a connect-disconnect means 108 is located in conduit 104 between valve 105 and the connection of conduit 103 to conduit 104. This permits the interior of wall 13 of double walled container 30A and annular chamber 43 to be placed under a vacuum when desired.

The exterior end of drain pipe 23 is connected by a flexible convoluted metal hose 118 to a drain line 120 extending through the energy absorbing wall 8 and the reinforced concrete wall 4. The convoluted metal hose 118 has a connect-disconnect means 35 at one end connecting it with the outer end of drain pipe 23 and a connect-disconnect means 37 at the other end connecting it with the end of drain line 120 within energy absorbing wall 8. A remotely operated valve 25 controls drain flow from within wall 13 of the cryogenic double walled container 30A. Pressure vents 117 (with associated check valve) and 115, provide venting for filling the interior of inner wall 13 and annular chamber 41, respectively.

With the apparatus as shown in FIG. 1, it can be used to provide cryogenic proof testing of a rotating part as follows: With all of the valves closed;

(1) place interior of inner container wall 13 at a vacuum of 0.3 to 0.5 mm mercury by opening valves 105 and 109. Close valve 109 and open valve 100 to fill this same volume with gaseous dry nitrogen (GN$_2$) to atmospheric pressure. Repeat this two-step sequence as necessary to remove moisture from the cryogenic spin testing chamber 14A;

(2) place annular chamber 43 under a vacuum of 0.3 to 0.5 mm mercury by opening then closing valves 105 and 107;

(3) with valve 105 closed, open valves 86 and 94 and fill the interior of inner wall 13 of double walled container 30A with liquid nitrogen (LN$_2$) to a predetermined level (observing the liquid nitrogen (LN$_2$) level through porthole in cover 16A, not shown) above disc 66 (venting automatically through vent 117 with its check valve);

(4) close valve 94 and open valve 84 and fill the space between inner wall 13 and outer wall 15, to desired level as indicated by cryogenic fluid level indicator 74, with liquid nitrogen (LN$_2$);

(5) close valve 84 and open valve 101 and fill annular chamber 41 with liquid nitrogen (LN$_2$) (vent as necessary); close valve 101;

(6) soak disc 66 for a time sufficient to achieve a stabilized cryogenic temperature throughout the test disc 66, maintaining a predetermined liquid nitrogen level above disc 66 by opening valves 86 and 94 as needed;

(7) with valve 94 closed, open valve 25 and drain liquid nitrogen (LN$_2$) from within the inner wall 13 of the double walled container 30A; when liquid nitrogen (LN$_2$) level is below the disc, spin disc at approximately 300–400 rpm for a few seconds to force residual liquid nitrogen (LN$_2$) off the test disc 66;

(8) after completion of drain, close valve 25 and open valves 105 and 109 and place vacuum within inner wall 13 of double walled container 30A of 1 mm mercury or better;

(9) spin disc 66 to a predetermined test speed (hold for predetermined time period if desired).

After the cryogenic proof testing of a rotating part has been completed, the apparatus 1A can be torn down in the following manner to remove the test disc and replace it by the next part to be tested:

(1) close valve 105 and open valve 100 filling inside of inner wall 13 of double walled container 30A with gaseous dry nitrogen (GN$_2$) to atmospheric pressure (conduit 117 and associated valve venting) and flow gaseous nitrogen (GN$_2$) until the interior of container 30A reads warmer than 32° F. (0° C.); using heated gaseous nitrogen (GN$_2$) optional;

(2) move lock pins 18 to their unlocked position;

(3) disconnect conduits 82, 96 and 104;

(4) lift chamber 14A out of the spin pit 2 by hooking onto lifting eyes 17 on cover 16A;

(5) when the connect-disconnect means 35 can be reached, disconnect the drain pipe 23 from the convoluted metal hose 118;

(6) completely remove chamber 14A out of the spin pit 2;

(7) remove sufficient insulation 112A to unbolt annular ring 21 from cover 16A;

(8) separate unbolted cover 16A and annular ring 21, removing double walled container and connected parts from the cover 16A exposing the spin arbor 64 and test disc 66;

(9) remove test disc 66 and spin arbor 64 from shaft 62.

Reverse order of teardown for subsequent test setup.

We claim:

1. A method of cryogenic proof testing a rotatable metallic part which has characteristics of high strength and low fracture toughness is comprised of:
    (1) placing said part at a cryogenic temperature, which increases ultimate tensile strength and decreases fracture toughness to reduce critical flaw size necessary for part fracture;
    (2) rotating said part at said cryogenic temperature and at a speed equivalent to a stress level not to exceed 0.2% yield strength of the metallic part so that no detrimental permanent deformation of said part occurs while producing a stress on said part to fracture said part at or above the reduced critical flaw size.

2. A method as set forth in claim 1 wherein step (2) the part is rotated at a speed equivalent to approximately 0.2% yield strength of the metallic part.

3. A method of cryogenic proof testing a rotatable metallic part as set forth in claim 1 wherein the cryogenic temperature is −320° F. (−195.55° C.).

4. A method as set forth in claim 1 wherein step (2) said part is rotated in a vacuum.

5. A method as set forth in claim 1 wherein step (1) said part is immersed in a cryogenic liquid until a desired cryogenic temperature is reached in said part, then said part is separated from said cryogenic liquid; wherein step (2) said part is rotated in a vacuum.

6. A method as set forth in claim 1 including
    (3) bringing said part to room temperature, said part retaining beneficial residual stresses to give it a life benefit, and retaining no critical flaw above the reduced critical flaw size which would cause fracture at the speed rotated.

* * * * *